United States Patent [19]
Yamano

[11] Patent Number: 5,729,207
[45] Date of Patent: Mar. 17, 1998

[54] CORROSIVE GAS DETECTING SENSOR

[75] Inventor: Naoto Yamano, Tokyo, Japan

[73] Assignee: Hochiki Corporation, Tokyo, Japan

[21] Appl. No.: 774,073

[22] Filed: Dec. 23, 1996

[30] Foreign Application Priority Data

Dec. 26, 1995 [JP] Japan .................. 7-339725

[51] Int. Cl.[6] .................................. G08B 17/10
[52] U.S. Cl. .................. 340/628; 340/630; 340/632; 73/24.01
[58] Field of Search .................. 340/628, 632, 340/633, 634, 630; 73/23, 23.4, 24.01, 863.25

[56] References Cited

U.S. PATENT DOCUMENTS

| | | | |
|---|---|---|---|
| 3,710,365 | 1/1973 | Barnes | 340/630 |
| 3,930,247 | 12/1975 | Hurd | 340/237.5 |
| 4,329,870 | 5/1982 | Farmer | 73/23 |
| 4,505,146 | 3/1985 | Miners | 73/19 |
| 5,065,140 | 11/1991 | Neuburger | 340/634 |
| 5,280,273 | 1/1994 | Goldstein | 340/628 |
| 5,404,762 | 4/1995 | Rodgers et al. | 73/863.25 |

*Primary Examiner*—Jeffery Hofsass
*Assistant Examiner*—Davetta Woods
*Attorney, Agent, or Firm*—Sughrue, Mion, Zinn, Macpeak & Seas, PLLC

[57] ABSTRACT

A corrosive gas detecting sensor has a cartridge, a sensor body, and a connecting unit. The cartridge has a sensor element and a memory device. The sensor element changes its characteristic property when the sensor element contacts a corrosive gas, and the memory stores an initial value of the characteristic property of the sensor element. The sensor body has a control unit which detects a change of the characteristic property of the sensor element when the cartridge is connected to the body and outputs an indication of a fire when a rate of the change exceeding a preset reference value, the cartridge is detachably attached to the sensor body. The connecting unit electrically connects the cartridge with the sensor body when the cartridge is attached to the sensor body.

5 Claims, 5 Drawing Sheets

CORROSIVE GAS DETECTING SENSOR

BACKGROUND OF THE INVENTION

1. Field of the Invention

The invention relates to a corrosive gas detecting sensor, particularly, relates to an HCl sensor which detects hydrogen chloride (HCl).

2. Description of the Related Art

As the development of the industry, disasters or accidents due to various kinds of flammable or toxic gasses, or oxygen deficiency occur more frequently. Even when only a trace of quantity of a corrosive gas exists in our living or working environment, particularly, the gas exerts various adverse effects on the human body and corrodes a metal and the like. Therefore, even a corrosive gas in low concentration causes production facilities, or an electronic circuit such as a computer to break down.

For example, a corrosive gas is generated when a power source cable of an electrical appliance is abnormally heated. Generally, a power source cable of an electrical appliance contains PVC (Polyvinyl Chloride) which is a flame-retardant material. It is well known that, when PVC is heated, HCl which is a corrosive gas is generated from chloride and hydrogen.

Known sensors for detecting HCl which is a corrosive gas include an HCl sensor of the quartz-crystal oscillator type. An HCl sensor of this kind uses a quartz-crystal oscillator as an oscillation element. For example, chrome film, gold film and a metal such as zinc or zinc compound film are deposited subsequently by evaporation on the both side of the center portion of the quartz-crystal oscillator. When the metal films are corroded by HCl, the weight of the film is increased and the oscillation frequency of the quartz-crystal oscillator is lowered. Consequently, HCl can be detected by detecting the change of the oscillation frequency.

FIG. 6 is a perspective view showing the appearance of a conventional HCl sensor using such a sensor element. As shown in the drawing, the HCl sensor comprises: a body 1; a circuit board 2 which is disposed inside the body 1; a sensor element 3 having a surface to which the above-mentioned process has been conducted; and an outer cover 4 which is fitted to the body 1 and covers the circuit board 2 and the sensor element 3. An EEPROM 5 is mounted on the circuit board 2. In the EEPROM 5, data such as the initial value of the number of vibration of the sensor element 3 are previously written. The circuit board 2 always compares the rate of change of the oscillation frequency of the sensor element 3 with a reference value. When the rate of change exceeds the reference value, the circuit board outputs a signal indicative of a fire.

When a power source cable is overheated by a short circuit or the like, for example, HCl is generated. When the generated HCl enters the interior of the HCl sensor via the outer cover 4, the metal films deposited on the sensor element 3 are corroded to thereby lower the number of vibration of the sensor element 3. If the rate of change of the oscillation frequency due to the number of vibration exceeds the reference value, the circuit board 2 outputs the signal indicative of a fire.

In the conventional HCl sensor, the sensor element 3 cannot be reused. When the sensor element once operates or reaches the end of the life period, therefore, it must be replaced with a new one. However, the work of replacing the sensor element is difficult to do because of the following reasons.

(A) In order to replace the sensor element 3, the HCl sensor must be disassembled.

(B) If a finger contacts with a portion of the surface of the sensor element 3, the portion corrodes. Therefore, the sensor element 3 must be handled with care. In this case, when the sensor element 3 is mounted on the circuit board 2, the sensor element 3 is covered with a cap 6 (see FIG. 6) so that the sensor 3 is handled through the cap 6.

(C) The contents of the EEPROM 5 must be rewritten so as to correspond to the initial value of the number of vibration of the new sensor element 3. Consequently, the worker must always carry a ROM writer.

(D) Because of (A) to (C) above, the cost of labor is increased.

SUMMARY OF THE INVENTION

It is an object of the invention to provide a corrosive gas detecting sensor in which replacement of a sensor element can be conducted easily and rapidly even if the replace is performed at a place where the sensor is mounted.

A corrosive gas detecting sensor according to the present invention is comprised of: a cartridge having a sensor element and a memory device, the sensor element changing its characteristic property when the sensor element contacts a corrosive gas, the memory storing an initial value of the characteristic property of the sensor element; a sensor body having a control unit for detecting a change of the characteristic property of the sensor element when the cartridge is connected to the body and for outputting an indication of a fire when a rate of the change exceeding a preset reference value, the cartridge being detachably attached to the sensor body; and a connecting unit for electrically connecting the cartridge with the sensor body when the cartridge is attached to the sensor body.

According to the present invention, the cartridge in which the sensor element is integrated with the memory device storing the characteristic property of the sensor element is disposed so as to be detachable with respect to the sensor body. When the sensor element cannot be used anymore, therefore, the memory device can be replaced together with the sensor element with a fresh one. In replacement of the sensor element, consequently, it is not required to disassemble the body, to directly handle the sensor element itself, or to rewrite the contents of the memory device. As a result, replacement of the sensor element can be conducted easily and rapidly even in the field. A used cartridge may be returned to the factory, and replacement of the element may be conducted together with rewriting of the memory device, so that the cartridge is reused. Alternatively, a used cartridge may be disposed as it is.

PREFERRED EMBODIMENTS OF THE INVENTION

Hereinafter, embodiments of the invention will be described with reference to the accompanying drawings. As one example of a corrosive gas detecting sensor, an HCl sensor will be described in this embodiment.

A. Configuration of the HCl Sensor

Figure 1:
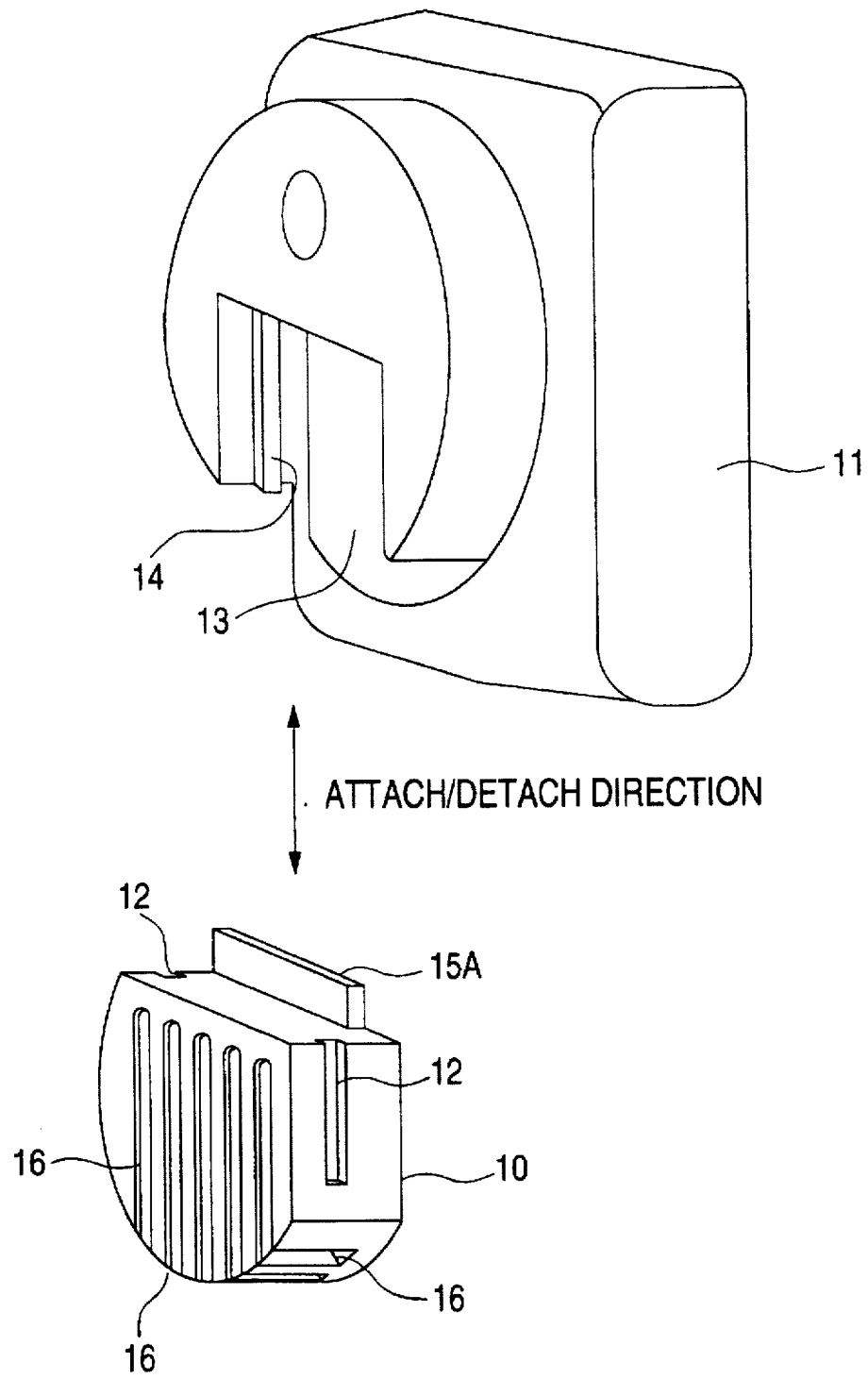
FIG. 1 is a perspective view showing an embodiment of the HCl sensor of the invention.
Figure 6:
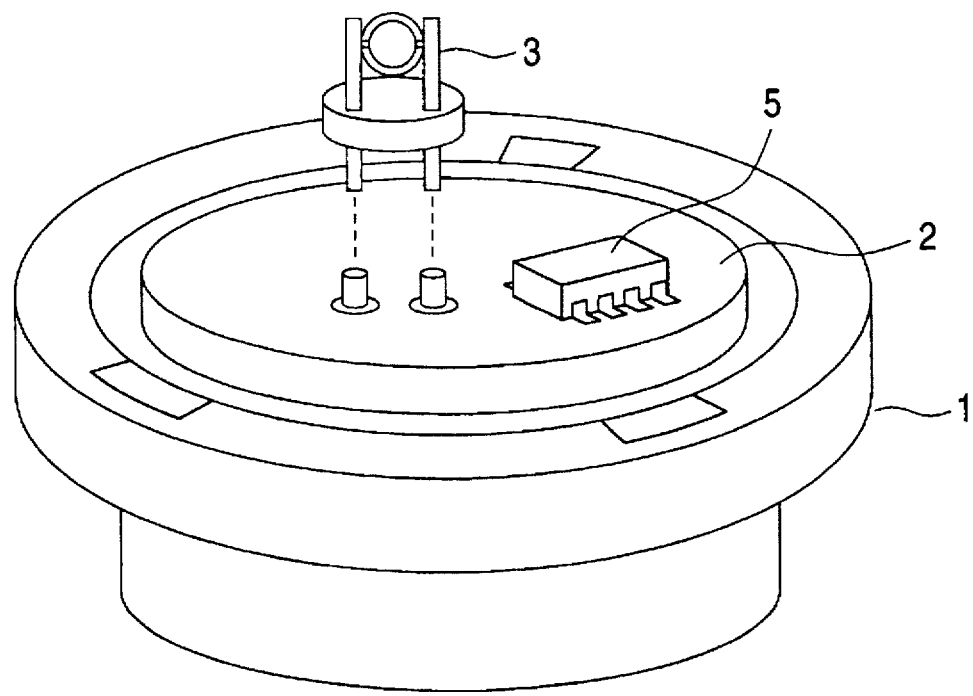
FIG. 6 is a perspective view showing the configuration of a prior art HCl sensor.

FIG. 1 is a perspective view showing an embodiment of the HCl sensor of the invention. In the drawings, the same portions as those of FIG. 6 are designated by the same reference numerals, and their description is omitted.

As shown in the drawing, the HCl sensor is constituted by: a cartridge 10 incorporating a sensor element 3 and an EEPROM 5 which stores the initial value of the number of vibration of the sensor element 3; and the sensor body 11 to which the cartridge 10 is attached. As illustrated, the cartridge 10 has a substantially semicircular shape in which the side and upper faces are flat. A thin long rail groove 12 is formed on each of the side faces so as to elongate in the insertion direction to the sensor body 11. When the cartridge 10 is attached to the sensor body 11, rails 14 formed on the side faces of a chamber 13 of the sensor body which houses the cartridge 10 are fittingly inserted into the rail grooves 12, respectively. A connector 15A is provided on the upper face of the cartridge 10. As described later, the connector 15A constitutes a part of a circuit board 15.

A plurality of thin long holes 16 elongating in the insertion direction to the sensor body 11 are formed in the cartridge 10. An HCl gas is introduced into the cartridge via the holes 16. In addition to the initial value of the number of vibration of the sensor element 3, fixed data (data which will not be changed) such as production and quality control data are previously written into the EEPROM 5 disposed in the cartridge 10. Data which may be changed are written into a memory device in a microcontroller 18 (see FIG. 4) of the sensor body 11.

In this way, the sensor element 3 and the EEPROM 5 which are integrated with each other are separated from the sensor body 11 and can be connected to the sensor body 11 through the connector 15A. Accordingly, the sensor element 3 can be replaced together with the EEPROM 5. Consequently, replacement of the sensor element 3 can be very easily conducted without using a ROM writer and paying attention to the handling of the sensor element 3. Because the sensor element 3 and the EEPROM 5 are low in price, even when the sensor element and the EEPROM are replaced in a bundle, therefore, the replacement cost is lower than the labor cost which is required in the conventional sensor for the works of replacing the sensor element 3 and writing data into the EEPROM 5.

Hereinafter, the configuration of the cartridge 10 and the sensor body 11 will be described in detail.

B. Configuration of the Cartridge 10

Figure 2:
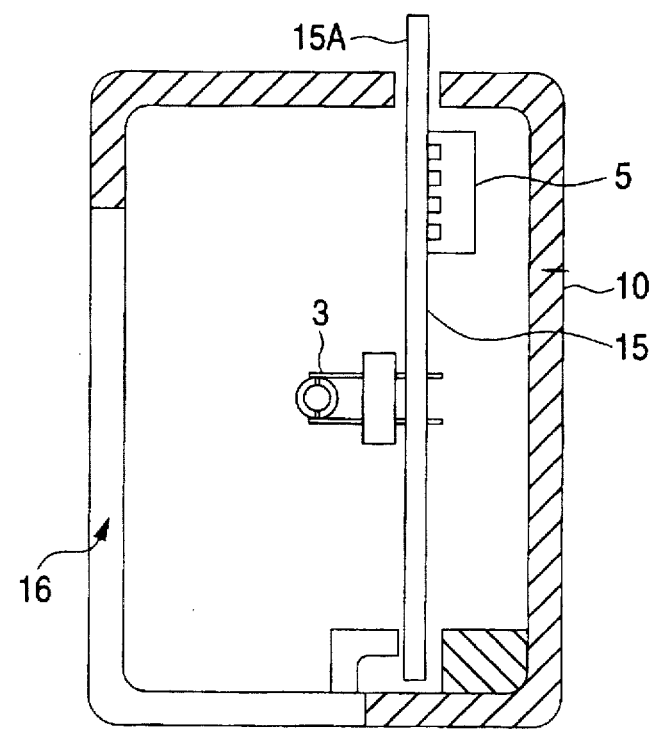
FIG. 2 is a longitudinal section view of a cartridge of the embodiment.

FIG. 2 is a longitudinal section view of the cartridge 10. The circuit board 15 is disposed in the cartridge 10. The sensor element 3 is mounted on one face of the circuit board, and the EEPROM 5 on the other face. The portion of the circuit board 15 which protrudes from the cartridge body to be exposed to the outside serves as the connector 15A. Terminals of the connector 15A are connected to the sensor element 3 and the EEPROM 5 via conductors.

Figure 3:
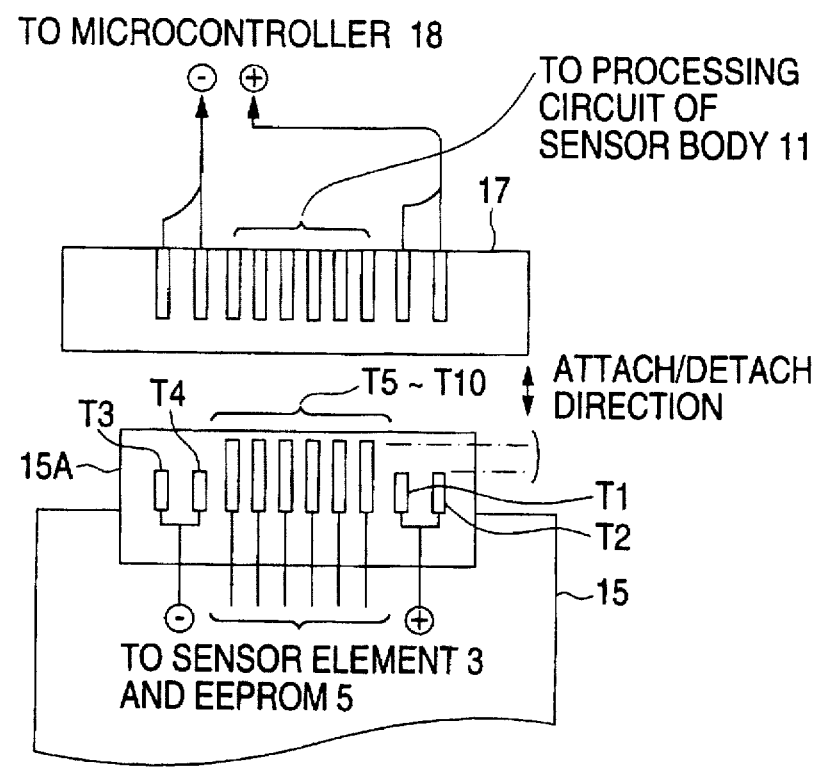
FIG. 3 is a view showing a portion of the embodiment where the cartridge is to be connected to the sensor body.

In the connector 15A of the circuit board 15, as shown in FIG. 3, two terminals $T_1$ and $T_2$, and $T_3$ and $T_4$ at each of the ends of the connector 15A are the power source terminals. These terminals are positioned so as to be recessed toward the cartridge body with respect to the other signal terminals $T_5$ to $T_{10}$. In other words, steps are formed between the power source terminals $T_1$ to $T_4$ and the signal terminals $T_5$ to $T_{10}$. The formation of the steps allows the signal line to be disconnected after the power source line of the sensor body is disconnected. The connector is configured in this way because, if the power source is turned off later, the sensor body 11 may output an abnormal signal when the signal terminals $T_5$ to $T_{10}$ are disengaged from a connector 17 of the sensor body. According to the configuration of the embodiment, the power source is first turned off and the signal line is then disconnected, thereby preventing the sensor body 11 from malfunctioning.

Because of the structure of the cartridge 10, it is impossible to put the cap 6 on the sensor element 3. Therefore, the sensor element may be affected by the atmosphere of the storage space and attention must be given to the storage. When the cartridge 10 is hermetically packed, it will not be affected by the atmosphere of the storage space. The cartridge may be packed together with silica gel, or an inert gas such as nitrogen may be filled in the package. Alternatively, the package may be formed as a vacuum pack.

C. Configuration of the Sensor Body 11

Figure 4:
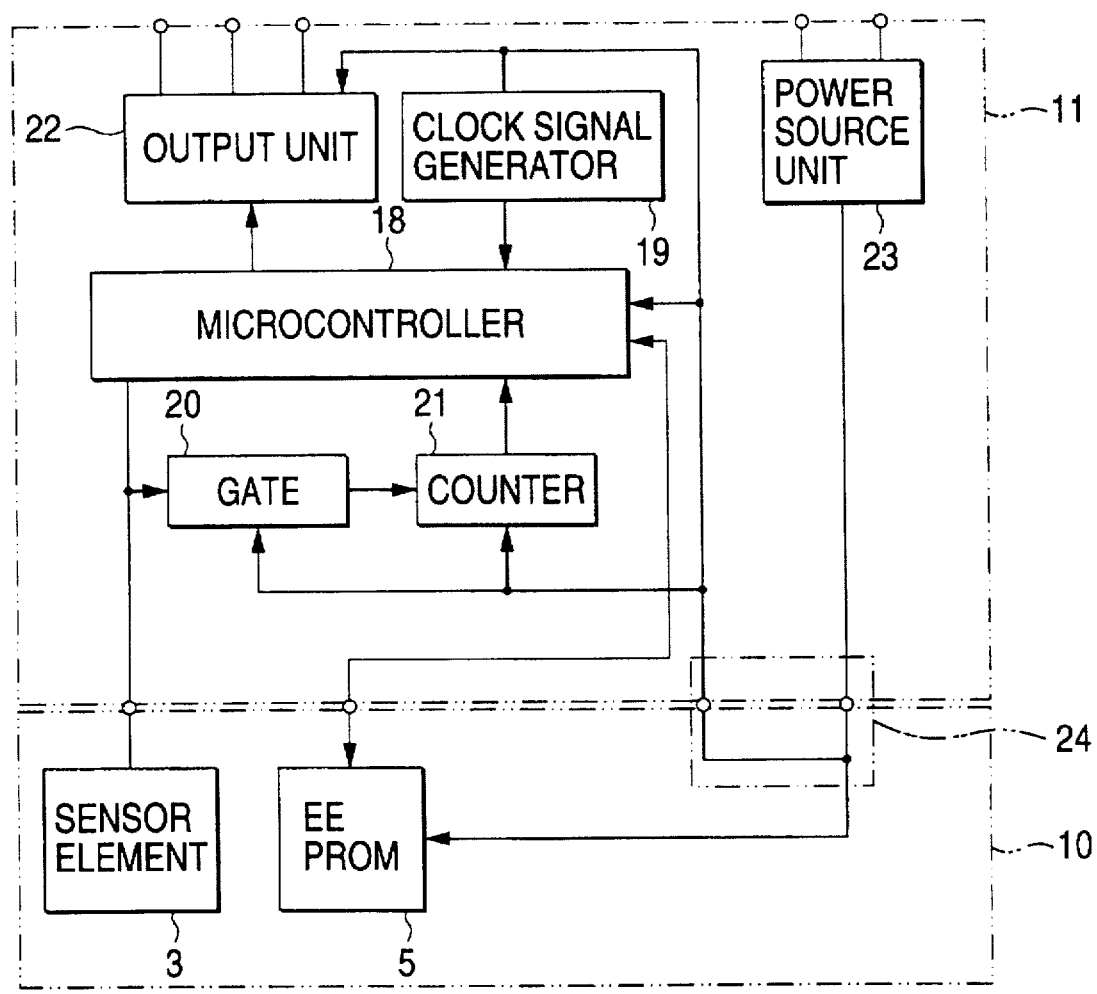
FIG. 4 is a block diagram showing the configuration of the sensor body of the embodiment.

FIG. 4 is a block diagram showing the configuration of the sensor body 11. In the drawing, the sensor body 11 is constituted by the microcontroller 18, a clock signal generator 19, a gate 20, a counter 21, an output unit 22, and a power source unit 23. The microcontroller 18 controls respective portions in accordance with programs which is stored in a memory therein. The clock signal generator 19 outputs a clock signal which is a base of the operation of the microcontroller 18. The gate 20 allows the signal from the sensor element 3 to pass therethrough only during a fixed period. The counter 21 counts the signal which has passed through the gate 20. The count number of the counter 21 is captured by the microcontroller 18.

The microcontroller 18 calculates the number of vibration of the sensor element 3 on the basis of the count number of the counter 21 and detects the rate of the change of the oscillation frequency to judge as to whether or not a fire occurs. In this case, if the rate of the change of the oscillation frequency is larger than a predetermined value, it is judged that a fire occurs, and a signal indicative of a fire is output via the output unit 22. The microcontroller 18 compares the calculated oscillation frequency with the initial value of the number of vibration of the sensor element 3 which is previously written into the EEPROM 5 of the cartridge 10, and judges the life period of the sensor element 3 on the basis of the difference between the frequency and the value. The microcontroller 18 monitors the voltage of the power source. If it is judged that the voltage is equal to or lower than a predetermined value, the microcontroller outputs a reset signal to respective portions.

The power source unit 23 converts a voltage (for example, 24 V) supplied from the outside into the voltage required in the cartridge 10 and the sensor body 11. The output of the power source unit 23 is supplied to respective portions of the sensor body 11 via the cartridge 10. As described above, the power source supply to the sensor body 11 is stopped by pulling out the cartridge 10 from the sensor body 11. In this case, the reference numeral 24 represents a switching unit configured by the power source terminals $T_1$ to $T_4$ of the connector 15A of the circuit board 15, and terminals (terminals corresponding to the power source terminals $T_1$ to $T_4$ of the connector 15A) of the connector 17 of the sensor body 11.

As described above, in the embodiment, the sensor element 3 is integrated with the EEPROM 5 which stores the initial value of the number of vibration of the sensor element 3, and the element and the memory are detachably attached to the sensor body 11. Accordingly, when the sensor element 3 once operates or reaches the end of the life period and cannot be further used, therefore, it can be replaced together with the EEPROM 5 with a new one. In replacement of the sensor element 3, consequently, it is not required to disassemble the body, to directly handle the sensor element 3 itself, or to rewrite the contents of the EEPROM 5. As a result, replacement of the sensor element 3 can be conducted easily and rapidly even in a place where the sensor is mounted.

Attachment of the cartridge 10 to the sensor body 11 causes the power source to be supplied to various portions of the sensor body 11 and the cartridge 10. Under the state where the cartridge 10 is not attached, therefore, the sensor body 11 is not powered, and hence the sensor body is prevented from wastefully consuming the power and also from being affected by external noises and the like.

When the cartridge 10 is pulled out from the sensor body 11, the power source line is first disconnected and the signal line is then disconnected. When the cartridge 10 is pulled out from the sensor body 11, therefore, the sensor body is prevented from malfunctioning.

Figure 5:
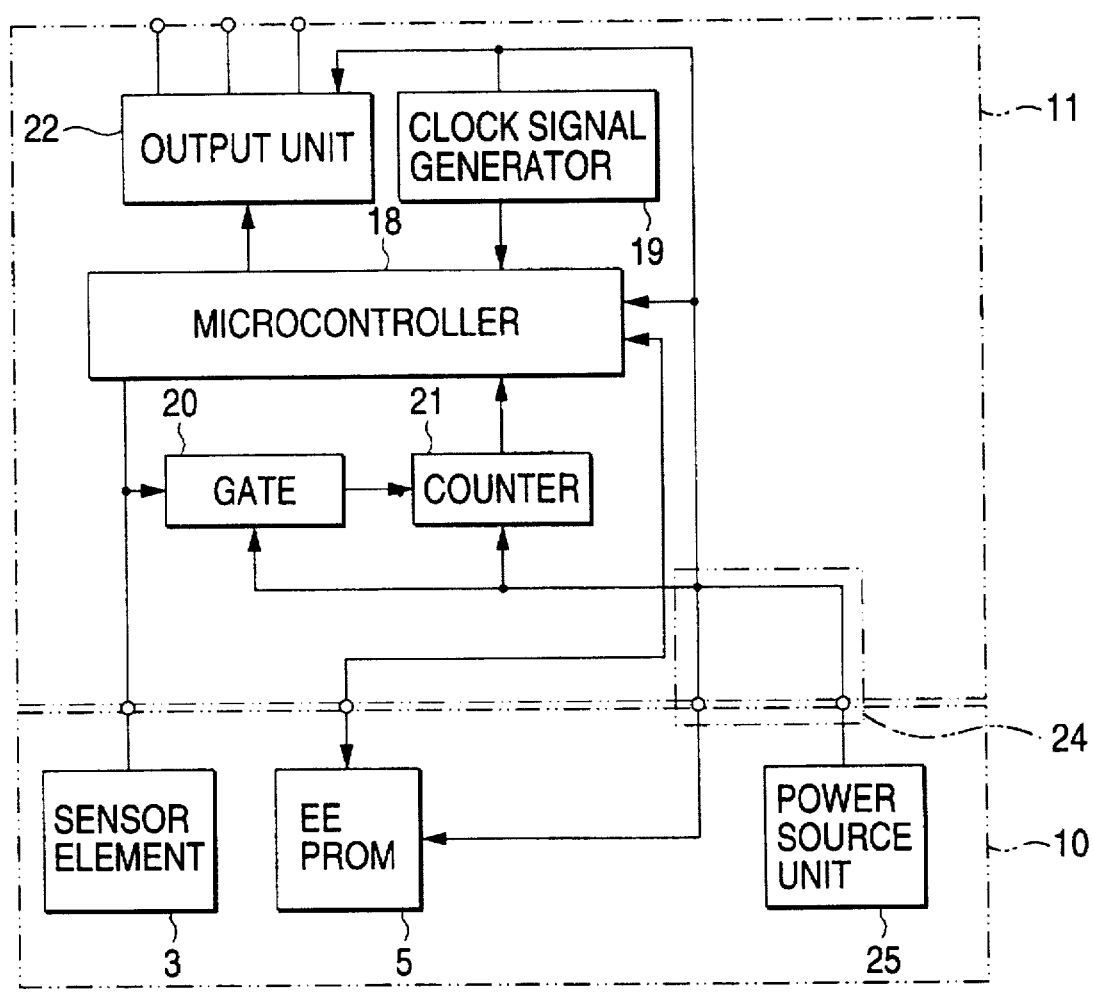
FIG. 5 is a block diagram showing the configuration of the sensor body of another embodiment of the HCl sensor of the invention.

In the embodiment described above, the sensor element 3 is integrated with the EEPROM 5. Alternatively, as shown in FIG. 5, a power source unit 25 may be added to the integrated unit. In the alternative, a lithium battery is preferably used as the power source of the power source unit 25. The output of the lithium battery is subjected to voltage conversion and then supplied to various portions of the sensor body 11 and the cartridge 10 via the switching unit.

The embodiment described above uses the EEPROM 5. The invention is not limited to this. Any kind of memory device may be used as far as it can store the initial value of the number of vibration of the sensor element 3.

In the embodiment, a sensor having a quartz-crystal oscillator is used as the sensor element 3. The invention is not limited to this. Any kind of sensor may be used as far as it can detect a corrosive gas.

In the corrosive gas detecting sensor according to the invention, the cartridge in which the sensor element is integrated with the memory device storing the characteristic property of the sensor element is disposed so as to be detachable with respect to the sensor body. In replacement of the sensor element, consequently, it is not required to disassemble the body, to directly handle the sensor element itself, or to rewrite the contents of the memory device. As a result, replacement of the sensor element can be conducted easily and rapidly even in the field.

Additionally, in the corrosive gas detecting sensor according to the invention, the power source supplying unit is disposed in the sensor body, and attachment of the cartridge to the sensor body causes the power to be supplied to various portions of the sensor body and the cartridge. Under the state where the cartridge is not attached, therefore, the sensor body is not powered, and hence the sensor body is prevented from wastefully consuming the power and also from being affected by external noises and the like.

Alternatively, in the corrosive gas detecting sensor according to the invention, the power source supplying unit is disposed in the cartridge, and attachment of the cartridge to the sensor body causes the power to be supplied to various portions of the sensor body and the cartridge. Under the state where the cartridge is not attached, therefore, the sensor body is not powered, and hence the sensor body is prevented from wastefully consuming the power and also from being affected by external noises and the like.

Further, in the corrosive gas detecting sensor according to the invention, when the cartridge is detached from the sensor body, the switching unit is turned off before the signal line is disconnected. Therefore, the sensor body is prevented from malfunctioning when the cartridge is detached from the sensor body.

What is claimed is:

1. A corrosive gas detecting sensor comprising:

a cartridge having a sensor element and a memory device, said sensor element changing its characteristic property when said sensor element contacts a corrosive gas, said memory storing an initial value of the characteristic property of said sensor element;

a sensor body having outputting means for detecting a change of the characteristic property of said sensor element when said cartridge is connected to said body and for outputting an indication of a fire when a rate of the change exceeding a preset reference value, said cartridge being detachably attached to said sensor body; and connecting means for electrically connecting said cartridge with said sensor body when said cartridge is attached to said sensor body.

2. A corrosive gas detecting sensor according to claim 1, further comprising power source supplying means;

wherein said connecting means has switching means which is turned on by attaching said cartridge to said sensor body, and which allows a power source to be supplied from said power source supplying means to said cartridge and said sensor body.

3. A corrosive gas detecting sensor according to claim 2, wherein said sensor body has said power source supplying means.

4. A corrosive gas detecting sensor according to claim 2, wherein said cartridge has said power source supplying means.

5. A corrosive gas detecting sensor according to claim 2, wherein, when said cartridge is detached from said sensor body, said switching means of said connecting means is turned off before a signal line in said connecting means is disconnected.

* * * * *